United States Patent
Algar et al.

(10) Patent No.: US 7,323,160 B2
(45) Date of Patent: *Jan. 29, 2008

(54) METHOD OF TREATING A PATIENT'S TEETH USING FLUORIDE RELEASING GLASS COMPOSITION

(75) Inventors: Brian Algar, Wales (GB); Jack Toumba, Leeds (GB); Martin Curzon, North Riding (GB)

(73) Assignee: Teldent Ltd., Denbigh, Denbigshire (GB)

( * ) Notice: Subject to any disclaimer, the term of this patent is extended or adjusted under 35 U.S.C. 154(b) by 591 days.

This patent is subject to a terminal disclaimer.

(21) Appl. No.: 10/726,218

(22) Filed: Dec. 2, 2003

(65) Prior Publication Data

US 2004/0234462 A1    Nov. 25, 2004

Related U.S. Application Data

(63) Continuation-in-part of application No. 10/069,143, filed as application No. PCT/GB00/03141 on Aug. 14, 2000, now Pat. No. 7,175,833.

(30) Foreign Application Priority Data

Aug. 14, 1999  (GB) ................................ 9919283.3

(51) Int. Cl.
| | |
|---|---|
| *A61K 8/42* | (2006.01) |
| *A61K 33/55* | (2006.01) |
| *A61Q 11/00* | (2006.01) |
| *A01N 59/26* | (2006.01) |
| *C03C 8/08* | (2006.01) |

(52) U.S. Cl. .................... 424/52; 424/57; 424/401; 424/435; 433/215; 433/217.1; 433/226; 433/228.1; 501/24; 501/25; 501/57; 501/58; 501/63; 501/72; 106/35

(58) Field of Classification Search .................... None
See application file for complete search history.

(56) References Cited

U.S. PATENT DOCUMENTS

| | | | |
|---|---|---|---|
| 4,920,082 A * | 4/1990 | Danielson .................... 501/59 |
| 5,098,304 A | 3/1992 | Scharf ........................ 433/215 |
| 5,306,338 A | 4/1994 | Tsunekawa .................. 106/35 |
| 5,427,768 A | 6/1995 | Tung ............................ 424/52 |
| 5,639,445 A | 6/1997 | Curtis et al. .................. 424/49 |
| 5,735,942 A | 4/1998 | Litkowski et al. ............ 106/35 |
| 5,762,950 A * | 6/1998 | Yli-Urpo et al. ............ 424/422 |
| 5,767,170 A | 6/1998 | Ibsen et al. ................... 522/81 |
| 5,891,233 A | 4/1999 | Salonen et al. ............... 106/35 |
| 6,030,220 A | 2/2000 | Karmaker et al. .......... 433/215 |
| 6,086,374 A | 7/2000 | Litkowski et al. ....... 433/217.1 |
| 6,200,137 B1 * | 3/2001 | Holand et al. ........... 433/212.1 |
| 6,280,863 B1 | 8/2001 | Frank et al. ................. 428/701 |
| 6,338,751 B1 | 1/2002 | Litkowski et al. ............ 106/35 |
| 6,455,609 B1 | 9/2002 | Rueggeberg et al. ....... 523/116 |
| 6,506,053 B2 | 1/2003 | Wiesel ....................... 433/215 |
| 2002/0037258 A1 | 3/2002 | Dodd et al. ................... 424/49 |

FOREIGN PATENT DOCUMENTS

| | | | |
|---|---|---|---|
| JP | H01-219038 | * | 9/1989 |
| JP | 05-194132 |   | 8/1993 |
| SU | 313794 | * | 9/1971 |
| WO | WO 0112567 |   | 2/2001 |

OTHER PUBLICATIONS

Chemical Abstract 92:153090, "Treatment of cervical hypersensitive dentin with glass ionomer cement" (1979).*
K.J. Toumba, "Alleviation of Dentine Sensitivity Using Glass Slow-Release Fluoride Devices: A Pilot Study." Division of Child Dental Health. Leeds Dental Institute, Leeds, U.K. Published Jun. 10, 2003.

* cited by examiner

*Primary Examiner*—Frederick Krass
(74) *Attorney, Agent, or Firm*—Workman Nydegger (57) ABSTRACT

A method of treating sensitive teeth includes (1) attaching a fluoride releasing glass composition to a person's tooth, and (2) allowing fluoride to be slowly released over time in order to reduce chronic and/or acute tooth sensitivity. A preferred glass composition comprises the general empirical formula given below, expressed in approximate weight percent of the element: P: 16-24, F: 5-30, O: 20-40 and at least one of Na, K, Li, or Al in an amount up to a total of about 40 weight percent and optionally, up to about 5 weight percent of boron and/or silicon.

26 Claims, 5 Drawing Sheets

Glass Compositions and Analyses

| Code | Na | P | Al | F | O | K | Ca | Mg | Na+K | F Analysed | Solubility | Melt Temp | Melt Time | Fluoride Retention |
|---|---|---|---|---|---|---|---|---|---|---|---|---|---|---|
| 1 | 21.23 | 20.67 | 6.76 | 19.48 | 31.86 | 0 | 0 | | 21.23 | 10.4 | 149 | 650C | 45MIN | 53.39 |
| 2 | 22.47 | 20.37 | 6.22 | 19.54 | 31.39 | 0 | 0 | | 22.47 | 10.97 | 503 | 650C | 45MIN | 56.14 |
| 3 | 23.68 | 20.08 | 5.69 | 19.6 | 30.94 | 0 | 0 | | 23.68 | 11.81 | 2920 | 650C | 45MIN | 60.26 |
| 4 | 21.54 | 21.18 | 6.26 | 18.37 | 32.64 | 0 | 0 | | 21.54 | 10.94 | 288 | 650C | 45MIN | 59.55 |
| 5 | 21.16 | 20.81 | 5.27 | 18.94 | 32.07 | 0 | 0 | 1.75 | 21.16 | 11.45 | 215 | 650C | 45MIN | 60.45 |
| 6 | 21.23 | 20.67 | 6.76 | 19.48 | 31.86 | 0 | 0 | | 21.23 | 11.42 | 149 | 650C | 45MIN | 58.62 |
| 7 | 21.13 | 20.87 | 4.55 | 18.67 | 32.17 | 0 | 0 | 2.59 | 21.13 | 11.78 | 305 | 650C | 45MIN | 63.10 |
| 8 | 22.88 | 20.27 | 6.04 | 19.56 | 31.25 | 0 | 0 | | 22.88 | 12.01 | 1385 | 650C | 45MIN | 61.40 |
| 9 | 23.28 | 20.17 | 5.87 | 19.59 | 31.09 | 0 | 0 | | 23.28 | 12.15 | 2513 | 650C | 45MIN | 62.02 |
| 10 | 23.21 | 19.68 | 6.22 | 20.56 | 30.33 | 0 | 0 | | 23.21 | 11 | 1816 | 650C | 45MIN | 53.50 |
| 11 | 22.72 | 20.31 | 6.11 | 19.56 | 31.3 | 0 | 0 | | 22.72 | 12.03 | 1962 | 650C | 45MIN | 61.50 |
| 12 | 22.91 | 19.16 | 6.72 | 21.68 | 29.53 | 0 | 0 | 0 | 22.91 | 14.11 | 1684 | 650C | 45MIN | 65.08 |
| 13 | 23.14 | 18.55 | 6.97 | 22.76 | 28.59 | 0 | 0 | 0 | 23.14 | 14.95 | 1715 | 650C | 45MIN | 65.69 |
| 14 | 21.9 | 20.13 | 5.27 | 19.94 | 31.02 | 0 | 0 | 1.75 | 21.9 | 13.22 | 405 | 650C | 45MIN | 66.30 |
| 15 | 22.63 | 19.44 | 5.26 | 20.94 | 29.97 | 0 | 0 | 1.75 | 22.63 | 14.06 | 661 | 650C | 45MIN | 67.14 |
| 16 | 22.13 | 18.76 | 5.26 | 22.3 | 28.92 | 0 | 0 | 2.62 | 22.13 | 14.79 | 685 | 650C | 45MIN | 66.32 |
| 17 | 21.83 | 18.24 | 5.75 | 23.42 | 28.12 | 0 | 0 | 2.64 | 21.83 | 14.86 | 560 | 650C | 45MIN | 63.45 |
| 18 | 14.92 | 20.67 | 6.76 | 18.04 | 31.86 | 7.75 | 0 | 0 | 22.67 | 11.15 | 61 | 650C | 45MIN | 61.81 |
| 19 | 14.29 | 19.79 | 6.25 | 19.71 | 30.5 | 7.68 | 0 | 1.78 | 21.97 | 12.42 | 100 | 650C | 45MIN | 63.01 |
| 20 | 22.07 | 21.09 | 6.01 | 18.34 | 32.5 | 0 | 0 | 0 | 22.07 | 11.2 | 194 | 650C | 45MIN | 61.07 |
| 21 | 21.85 | 21.68 | 5.76 | 17.29 | 33.42 | 0 | 0 | 0 | 21.85 | 10.2 | 574 | 650C | 45MIN | 58.99 |
| 22 | 18.95 | 19.44 | 5.26 | 20.1 | 29.97 | 4.53 | 0 | 1.75 | 23.48 | 12.6 | 389 | 650C | 45MIN | 62.69 |
| 23 | 21.23 | 20.67 | 6.76 | 19.48 | 31.86 | 0 | 0 | | 21.23 | 11 | 130 | 650C | 90MIN | 56.47 |
| 24 | 21.23 | 20.67 | 6.76 | 19.48 | 31.86 | 0 | 0 | | 21.23 | 10.2 | 79 | 650C | 180MIN | 52.36 |
| 25 | 18.95 | 19.44 | 5.26 | 20.1 | 29.97 | 4.53 | 0 | 1.75 | 23.48 | 13.4 | 466 | 650C | 45MIN | 66.72 |

FULL LIST OF GLASS COMPOSITIONS

| CODE | Na | P | Al | F | O | K | Ca | Mg | TOT. | Na+K | F Anal. | Sol. | Ret. | Devit. Grade |
|---|---|---|---|---|---|---|---|---|---|---|---|---|---|---|
| 63 | 19.91 | 18.54 | 8.87 | 24.1 | 28.58 | 0 | 0 | 0 | 100.0 | 19.91 | 10.7 | 45 | 44.40 | |
| 47 | 16.18 | 20.67 | 6.76 | 18.33 | 31.86 | 6.2 | 0 | 0 | 100.0 | 22.38 | 10.2 | 50 | 55.65 | |
| 18 | 14.92 | 20.67 | 6.76 | 18.04 | 31.86 | 7.75 | 0 | 0 | 100.0 | 22.67 | 11.15 | 61 | 61.81 | |
| 62 | 20.25 | 19.09 | 8.33 | 22.92 | 29.41 | 0 | 0 | 0 | 100.0 | 20.25 | 10.8 | 65 | 47.12 | |
| 34 | 20.58 | 19.62 | 7.8 | 21.75 | 30.25 | 0 | 0 | 0 | 100.0 | 20.58 | 11.9 | 78 | 54.71 | |
| 45 | 18.71 | 20.67 | 6.76 | 18.9 | 31.86 | 3.1 | 0 | 0 | 100.0 | 21.81 | 10.7 | 78 | 56.61 | |
| 46 | 17.44 | 20.67 | 6.76 | 18.61 | 31.86 | 4.65 | 0 | 0 | 100.0 | 22.09 | 10 | 79 | 53.73 | |
| 37 | 14.79 | 20.49 | 6.25 | 18.33 | 31.57 | 7.68 | 0 | 0.89 | 100.0 | 22.47 | 9.8 | 80 | 53.46 | |
| 44 | 19.97 | 20.67 | 6.76 | 19.19 | 31.86 | 1.55 | 0 | 0 | 100.0 | 21.52 | 10.6 | 80 | 55.24 | |
| 19 | 14.29 | 19.79 | 6.25 | 18.71 | 30.5 | 7.58 | 0 | 1.78 | 100.0 | 21.97 | 12.42 | 100 | 63.01 | |
| 71 | 18.97 | 20.11 | 6.85 | 19.72 | 31.01 | 3.34 | 0 | 0 | 100.0 | 22.31 | 10.6 | 100 | 53.75 | |
| 33 | 20.91 | 20.15 | 7.27 | 20.61 | 31.06 | 0 | 0 | 0 | 100.0 | 20.91 | 11.4 | 103 | 55.31 | |
| 69 | 11.66 | 18.35 | 7.11 | 20.46 | 28.33 | 13.87 | 0 | 0 | 100.0 | 25.53 | 11.5 | 107 | 56.15 | |
| 70 | 16.66 | 19.54 | 6.93 | 19.97 | 30.14 | 6.76 | 0 | 0 | 100.0 | 23.42 | 10.9 | 110 | 54.58 | |
| 38 | 14.66 | 20.3 | 6.76 | 18.61 | 31.29 | 7.51 | 0 | 1.76 | 100.0 | 22.27 | 10.2 | 128 | 54.81 | |
| 56 | 15.29 | 21.18 | 6.26 | 16.94 | 32.64 | 7.69 | 0 | 0 | 100.0 | 22.98 | 9.9 | 149 | 58.44 | |
| 1 | 21.23 | 20.67 | 6.76 | 19.48 | 31.86 | 0 | 0 | 0 | 100.0 | 21.23 | 10.65 | 158 | 54.67 | |
| 68 | 6.81 | 17.09 | 7.3 | 21.02 | 26.43 | 21.36 | 0 | 0 | 100.0 | 28.17 | 10.3 | 183 | 49.00 | 1 |
| 36 | 21.45 | 20.06 | 7.02 | 20.56 | 30.92 | 0 | 0 | 0 | 100.0 | 21.45 | 12.1 | 186 | 58.85 | |
| 39 | 14.16 | 19.62 | 6.76 | 19.7 | 30.23 | 7.61 | 1.16 | 1.76 | 100.0 | 21.77 | 10 | 189 | 60.76 | |
| 20 | 22.07 | 21.09 | 8.01 | 18.34 | 32.5 | 0 | 0 | 0 | 100.0 | 22.07 | 11.2 | 194 | 61.07 | |
| 35 | 21.67 | 19.45 | 7.27 | 21.65 | 29.97 | 0 | 0 | 0 | 100.0 | 21.67 | 12.4 | 196 | 57.27 | |
| 51 | 22.08 | 18.72 | 7.48 | 22.87 | 28.85 | 0 | 0 | 0 | 100.0 | 22.08 | 13.2 | 211 | 57.72 | |
| 5 | 21.16 | 20.81 | 5.27 | 18.94 | 32.07 | 0 | 0 | 1.75 | 100.0 | 21.16 | 11.45 | 215 | 60.45 | |
| 50 | 22.61 | 18.63 | 7.22 | 22.61 | 28.72 | 0 | 0 | 0 | 100.0 | 22.61 | 12.2 | 234 | 53.49 | |
| 4 | 21.54 | 21.18 | 6.26 | 18.37 | 32.64 | 0 | 0 | 0 | 100.0 | 21.54 | 10.94 | 268 | 59.55 | |
| 41 | 20.83 | 20.38 | 5.03 | 19.75 | 31.41 | 0 | 0 | 2.61 | 100.0 | 20.83 | 11.9 | 297 | 60.26 | |
| 7 | 21.13 | 20.87 | 4.55 | 18.67 | 32.17 | 0 | 0 | 2.59 | 100.0 | 21.13 | 11.78 | 305 | 63.10 | |
| 40 | 14.04 | 19.44 | 5.26 | 19.69 | 29.97 | 7.54 | 2.3 | 1.75 | 100.0 | 21.58 | 11.5 | 315 | 58.41 | |
| 25 | 19.27 | 19.95 | 4.79 | 19.02 | 30.75 | 4.49 | 0 | 1.73 | 100.0 | 23.76 | 11.07 | 370 | 58.20 | |
| 72 | 22.11 | 19.53 | 5.51 | 20.99 | 30.1 | 0 | 0 | 1.76 | 100.0 | 22.11 | 11.9 | 372 | 56.69 | |
| 14 | 21.9 | 20.13 | 5.27 | 19.94 | 31.02 | 0 | 0 | 1.75 | 100.0 | 21.9 | 12.9 | 385 | 64.69 | 1 |
| 22 | 18.95 | 19.44 | 5.26 | 20.1 | 29.97 | 4.53 | 0 | 1.75 | 100.0 | 23.48 | 12.6 | 389 | 62.69 | 1 |
| 65 | 13.05 | 18.08 | 5.26 | 22.21 | 27.87 | 6.03 | 5.75 | 1.75 | 100.0 | 19.08 | 13.5 | 401 | 60.78 | |
| 57 | 15.15 | 20.99 | 5.76 | 16.6 | 32.36 | 9.14 | 0 | 0 | 100.0 | 24.29 | 9.4 | 405 | 56.65 | |
| 42 | 20.64 | 20.2 | 4.55 | 19.74 | 31.14 | 0 | 1.14 | 2.59 | 100.0 | 20.64 | 11.6 | 410 | 58.76 | |
| 64 | 13.05 | 18.08 | 5.26 | 21.85 | 27.87 | 7.54 | 4.6 | 1.75 | 100.0 | 20.59 | 12.1 | 413 | 55.38 | |
| 59 | 21.11 | 22.37 | 5.77 | 16.27 | 34.48 | 0 | 0 | 0 | 100.0 | 21.11 | 7.8 | 435 | 47.94 | |
| 31 | 19.27 | 19.95 | 4.79 | 18.74 | 30.75 | 4.49 | 1.14 | 0.87 | 100.0 | 23.76 | 11.34 | 499 | 60.51 | |
| 2 | 22.47 | 20.37 | 6.22 | 19.54 | 31.39 | 0 | 0 | 0 | 100.0 | 22.47 | 10.97 | 503 | 56.14 | |
| 26 | 19.59 | 20.45 | 4.32 | 17.95 | 31.52 | 4.45 | 0 | 1.72 | 100.0 | 24.04 | 10.73 | 570 | 59.78 | |
| 43 | 20.16 | 19.53 | 4.55 | 20.81 | 30.1 | 0 | 2.27 | 2.59 | 100.0 | 20.16 | 12.1 | 570 | 58.15 | |
| 21 | 21.85 | 21.68 | 5.76 | 17.29 | 33.42 | 0 | 0 | 0 | 100.0 | 21.85 | 10.2 | 574 | 58.99 | |
| 80 | 23.62 | 20.15 | 4.97 | 19.33 | 31.06 | 0 | 0 | 0.86 | 100.0 | 23.62 | 10.2 | 631 | 52.77 | 1 |
| 30 | 19.27 | 19.95 | 4.79 | 18.47 | 30.75 | 4.49 | 2.28 | 0 | 100.0 | 23.76 | 10.99 | 699 | 59.50 | |
| 79 | 23.62 | 20.15 | 4.97 | 19.06 | 31.06 | 0 | 1.13 | 0 | 100.0 | 23.62 | 9.1 | 785 | 47.74 | 1 |
| 28 | 18.78 | 19.28 | 4.78 | 19.73 | 29.71 | 5.98 | 0 | 1.73 | 100.0 | 24.76 | 11.2 | 851 | 56.77 | 1 |
| 27 | 19.39 | 19.28 | 4.78 | 19.87 | 29.71 | 5.23 | 0 | 1.73 | 100.0 | 24.62 | 12.9 | 860 | 64.92 | 1 |
| 32 | 18.78 | 19.27 | 4.78 | 19.19 | 29.71 | 5.98 | 2.28 | 0 | 100.0 | 24.76 | 12.4 | 949 | 64.62 | 1 |
| 29 | 19.11 | 19.79 | 4.31 | 18.66 | 30.48 | 5.93 | 0 | 1.72 | 100.0 | 25.04 | 12.23 | 1006 | 65.54 | |
| 13 | 23.14 | 18.55 | 6.97 | 22.76 | 28.59 | 0 | 0 | 0 | 100.0 | 23.14 | 14.2 | 1038 | 62.39 | |
| 75 | 19.34 | 20.19 | 3.62 | 18.37 | 31.11 | 4.4 | 0 | 2.97 | 100.0 | 23.74 | 11.8 | 1205 | 64.24 | 1 |
| 52 | 14.49 | 20.08 | 5.69 | 17.5 | 30.94 | 11.29 | 0 | 0 | 100.0 | 25.78 | 11 | 1315 | 62.86 | |
| 8 | 22.88 | 20.27 | 6.04 | 19.56 | 31.25 | 0 | 0 | 0 | 100.0 | 22.88 | 12.01 | 1385 | 61.40 | |
| 12 | 22.91 | 19.16 | 6.72 | 21.68 | 29.53 | 0 | 0 | 0 | 100.0 | 22.91 | 14.11 | 1664 | 65.08 | |
| 10 | 23.21 | 19.68 | 6.22 | 20.56 | 30.33 | 0 | 0 | 0 | 100.0 | 23.21 | 11 | 1816 | 53.50 | |
| 58 | 22.16 | 22.17 | 5.28 | 16.22 | 34.16 | 0 | 0 | 0 | 100.0 | 22.16 | 9.2 | 1841 | 56.72 | |
| 11 | 22.72 | 20.31 | 6.11 | 19.56 | 31.3 | 0 | 0 | 0 | 100.0 | 22.72 | 12.03 | 1962 | 61.50 | |
| 9 | 23.28 | 20.17 | 5.87 | 19.59 | 31.09 | 0 | 0 | 0 | 100.0 | 23.28 | 12.15 | 2513 | 62.02 | |
| 3 | 23.68 | 20.08 | 5.69 | 19.6 | 30.94 | 0 | 0 | 0 | 100.0 | 23.68 | 11.81 | 2920 | 60.26 | |
| 76 | 23.83 | 20.33 | 5.45 | 19.06 | 31.33 | 0 | 0 | 0 | 100.0 | 23.83 | 10.9 | 6558 | 57.19 | |
| 77 | 23.97 | 20.56 | 5.21 | 18.53 | 31.72 | 0 | 0 | 0 | 100.0 | 23.97 | 8.3 | 7918 | 44.79 | |
| 78 | 24.19 | 20.82 | 4.97 | 18 | 32.1 | 0 | 0 | 0 | 100.1 | 24.19 | 9.8 | 9285 | 54.44 | |
| 53 | 24.25 | 21.07 | 4.74 | 17.47 | 32.47 | 0 | 0 | 0 | 100.0 | 24.25 | 10.7 | 10429 | 61.25 | |
| 55 | 22.63 | 17.85 | 6.96 | 23.49 | 27.52 | 1.54 | 0 | 0 | 100.0 | 24.17 | | | | 2 |
| 60 | 19.26 | 20.1 | 3.39 | 17.97 | 30.98 | 4.38 | 2.23 | 1.69 | 100.0 | 23.64 | | | | 2 |
| 61 | 19.26 | 20.1 | 3.39 | 18.5 | 30.98 | 4.38 | 0 | 3.38 | 100.0 | 23.64 | | | | 2 |
| 66 | 19.18 | 18.18 | 4.54 | 23.48 | 28.03 | 0 | 2.27 | 4.31 | 100.0 | 19.18 | | | | 2 |
| 67 | 17.73 | 17.85 | 4.54 | 24.5 | 27.51 | 0 | 2.27 | 5.6 | 100.0 | 17.73 | | | | 2 |
| 73 | 23.66 | 18.47 | 6.71 | 22.7 | 28.46 | 0 | 0 | 0 | 100.0 | 23.66 | | | | 2 |
| 74 | 22.83 | 18.01 | 7.48 | 23.81 | 27.76 | 0 | 0 | 0 | 100.0 | 22.83 | | | | 2 |
| 81 | 23.42 | 19.98 | 4.5 | 19.06 | 30.79 | 0 | 2.25 | 0 | 100.0 | 23.42 | | | | 2 |
| 15 | 22.63 | 19.44 | 5.26 | 20.94 | 29.97 | 0 | 0 | 1.75 | 100.0 | 22.63 | | | | 3 |
| 16 | 22.13 | 18.76 | 5.26 | 22.3 | 28.82 | 0 | 0 | 2.62 | 100.0 | 22.13 | | | | 3 |
| 48 | 23.14 | 19.36 | 5.02 | 20.9 | 29.84 | 0 | 0 | 1.74 | 100.0 | 23.14 | | | | 3 |
| 54 | 23.69 | 17.85 | 6.96 | 23.78 | 27.52 | 0 | 0 | 0 | 100.0 | 23.69 | | | | 3 |
| 82 | 23.42 | 19.98 | 4.5 | 19.6 | 30.79 | 0 | 0 | 1.71 | 100.0 | 23.42 | | | | 3 |
| 17 | 21.83 | 18.24 | 5.75 | 23.42 | 28.12 | 0 | 0 | 2.64 | 100.0 | 21.83 | | | | 4 |
| 49 | 23.65 | 19.28 | 4.78 | 20.85 | 29.71 | 0 | 0 | 1.73 | 100.0 | 23.65 | | | | 4 |

Fig. 5

METHOD OF TREATING A PATIENT'S TEETH USING FLUORIDE RELEASING GLASS COMPOSITION

RELATED APPLICATIONS

The present application is a continuation-in-part of U.S. patent application Ser. No. 10/069,143, with an effective filing date of Jul. 25, 2002 entitled "A Glass Composition," now U.S. Pat. No. 7,175,833 which is a national phase application under 35 U.S.C. § 371 of PCT/GB00/03141, filed Aug. 14, 2000 entitled "A Glass Composition," which claims priority to Great Britain application number 9919283.3, filed Aug. 14, 1999, each of which is incorporated herein by reference in its entirety.

BACKGROUND OF THE INVENTION

1. The Field of the Invention

The present invention relates to fluoride containing glass compositions that may be used not only to help prevent demineralization of teeth, but also to alleviate pain and/or sensitivity of a patient's teeth.

2. The Relevant Technology

Dental caries consist of demineralization of a tooth caused by bacteria. In the early stages of caries a white spot develops on the tooth and if the disease is not halted and reversed, the enamel surface breaks down to form a lesion. This can then lead to decay and eventually, a fractured tooth. It is well known that development of dental caries may be reduced by means of various factors, such as diet and oral hygiene measures, anti-microbial treatments and the provision of fluoride to the teeth.

Tooth sensitivity is also a common problem affecting children and adults. Generally, tooth sensitivity may be caused by gingival recession, dentine exposure due to erosion or abrasion, or periodontal surgery that includes root planning. Such conditions leave the dentinal tubules of the tissue susceptible to irritation by chemical, bacterial, mechanical or thermal stimuli. Examples of stimuli include heat, cold, and sweet foods. It is believed that tooth sensitivity is the result of nerve endings of the dental pulp being excited by fluid flow through the exposed dentinal tubules.

Treatments directed to alleviating pain associated with sensitive teeth have generally focused on blocking access to the dentinal tubules so as to prevent stimuli from causing pain and sensitivity. Many treatments have been developed which include application of inorganic or organic components designed to plug or otherwise block dentinal tubules for a limited time. A disadvantage of such treatments is that normal habits such as eating certain foods (e.g. foods with a high acid content) or brushing can negate the treatment. Recently, testing has revealed that increased fluoride levels within the mouth may also be used as a treatment for tooth sensitivity (Toumba and Andreadis).

Current methods for administering fluoride for caries prevention include the fluoridation of drinking water, the ingestion of fluoride tablets, the incorporation of fluoride into mouth washes, toothpastes, and foods, the topical application of fluoride solutions, gels and varnishes and recently, the incorporation of fluoride in dental materials and devices.

Evidence supports the concept of frequent applications of relatively low concentrations of fluoride ions for the prevention of caries and the treatment of sensitive teeth. A sustained and controlled release delivery system could help to achieve this goal.

Although glass compositions that release fluoride ions in the mouth have proven useful for caries prevention, they have also exhibited various difficulties. Silicate glasses from which fluoride can be slowly leached have been disclosed in U.S. Pat. No. 4,920,082 and WO 88105652, but these glasses generally exhibit low fluoride retention, while requiring high batch melting temperatures. The use of phosphate as a glass former has been known for many years. However, the disadvantage of these glasses is that they are easily attacked by water. This property has been exploited for the development of soluble glasses for use in animal health releasing copper, cobalt, and selenium to ruminant animals over 6 to 12 months as the glass dissolves (GB Pat. No. 2116424). A more slowly dissolving glass has been used to provide copper ions in an anti-fouling paint for use on ships. This glass was formulated to dissolve over 5 years (EP App. No. 94906287.1).

Hence, existing glass compositions have not been entirely satisfactory for use in slow fluoride release intra-oral devices. The low retention of many fluoride containing glasses means that the release of fluoride is not maintained over a sufficiently long period of time. In addition, the low retention would require a relatively large piece of glass to be fixed to the tooth of the patient to provide sufficient levels of fluoride release into the mouth. This would be obtrusive and reduce the appeal of the device to a patient.

BRIEF SUMMARY OF THE INVENTION

The present invention relates generally to a method of treating sensitive teeth with a fluoride glass composition. The method involves: (1) attaching a fluoride releasing glass composition to a person's tooth; and (2) allowing fluoride to be slowly released over time in order to reduce chronic and/or acute tooth sensitivity. Because the method relies on release of fluoride into the oral cavity, the method also prevents future pain associated with dental caries by preventing demineralization and maintaining strong enamel.

The fluoride glass composition has the general empirical formula of about 16 to about 24 weight percent phosphorus, about 5 to about 30 weight percent fluorine, and about 20 to about 40 weight percent oxygen, and at least one of sodium, potassium, lithium, or aluminum in an amount up to a total of about 40 weight percent, and optionally, up to about 5 weight percent of boron and/or silicon. Fluorides and/or oxides of glass modifiers, such as aluminum, calcium, and magnesium, may be included in the composition. The fluoride ions are preferably included as compounds such as $AlF_3$, $NaHF_2$, $NaF$, $CaF_2$, $MgF_2$ or $KF$.

Other glass modifiers, such as calcium, magnesium, and zinc may be included in the composition in an amount between about 0 and about 10 weight percent, more preferably less than about 5 weight percent.

The glass compositions may be used for alleviating pain and/or sensitivity of teeth in addition to any effect that the fluoride releasing glass compositions may have in preventing dental caries. The compositions may be attached to a tooth to provide slow-fluoride releasing devices for releasing fluoride into the saliva of an individual.

The glass compositions preferably provide a fluoride retention of at least 45% at a melting temperature of 650° C. over 45 minutes, more preferably at least 60%. Preferably, the glass composition has a low solubility rate thereby allowing fluoride release from the composition for a period of 12-36 months. The solubility of the composition may range from 5-10,000. The required solubility of the glass composition will depend upon the duration of fluoride release required. For example, if the composition is required to release fluoride over a long period, such as 1-2 years, the solubility is preferably 100-1100, more preferably 100-1000. However, if fluoride need only be released for a shorter period, such as a few weeks or months, a more soluble glass may be used, for example having solubility of up to 10,000.

The glass compositions may be attached to a tooth, for example being attached to a rear molar using standard dental cement or as a powder for adding to dental materials, such as dental amalgams, thereby providing means to supplement fluoride release into saliva to assist in the prevention or reduction of dental caries. The powder may be included in a number of other dental materials, such as fissure sealant resins or composite bonding materials to cement bonds and brackets in orthodontic appliances. Powder applications may use glass compositions that are less soluble than those that are attached directly to a tooth, for example having a solubility of 5-100. Such compositions may contain higher levels of glass modifiers and lower alkali levels than those compositions that have a higher solubility.

According to one embodiment, the composition includes a combined weight percent of at least about 16% of sodium and potassium, more preferably about 19 to about 26 weight percent. Aluminum is preferably included in an amount of at least about 3 weight percent, more preferably about 4 weight percent, most preferably about 4 to about 10 weight percent.

The composition preferably has at least about 25 weight percent oxygen, more preferably about 25 to about 35 weight percent oxygen, at least about 16 weight percent phosphorus, more preferably about 17 to about 23 weight percent, and at least about 12 weight percent F, more preferably about 15 to about 25 weight percent. Silicon or boron may replace some of the phosphorus as glass formers. However, preferably only amounts of up to about 5 weight percent are included to prevent the glass solubility from being unacceptably modified.

The phosphorus may be included in the composition as an oxide, such as $P_2O_5$. The alkali metals may be included as, for example, their oxides or fluorides.

It is to be appreciated that the glass compositions used should preferably have no, or minimal, devitrification/phase separation. The person skilled in the art of glass making would vary the oxides listed to reduce the tendency of the composition to devitrify in a particular case. For example, the skilled person would know that there are many influences on the tendency of glass compositions to devitrify. For example, glass components with low levels of phosphorus tend to be prone to devitrification and glasses with high levels of magnesium have poor resistance to devitrification. Fluoride glasses may also be prone to phase separation.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 1 is a table illustrating the percentage fluoride retention of 25 samples investigated in Example 1;

FIG. 5 is a table illustrating the solubility, percentage fluoride retention and extent of devitrification of 82 exemplary glass compositions according to the present invention.

DETAILED DESCRIPTION OF THE PREFERRED EMBODIMENTS

I. Introduction

The inventive method involves attaching a fluoride releasing glass composition to a person's tooth, and then allowing fluoride to be slowly released over time in order to reduce chronic and/or acute tooth sensitivity. According to a preferred embodiment, the fluoride releasing glass composition comprises, on an empirical basis, about 16-24 weight percent phosphorus, about 5-30 weight percent fluorine, about 20-40 weight percent oxygen, and at least one of sodium, potassium, lithium, or aluminum in an amount up to a total of about 40 weight percent and optionally, up to about 5 weight percent boron and/or silicon.

Exemplary glass compositions will now be further illustrated by means of the following examples in which Example 1 investigates the percentage fluoride retention for 25 samples of glass compositions according to the present invention; Example 2 investigates the percentage of fluoride in saliva following attachment of a glass composition of the present invention to a patient's tooth; Example 3 investigates the way that percentage fluoride in slow-releasing glass devices formed from glass compositions according to the present invention affects fluoride release; Example 4 investigates the effect of the location of the fluoride-releasing device on fluoride levels in saliva in adult human volunteers; Example 5 investigates the effectiveness of powdered glass compositions according to the present invention in releasing fluoride into saliva; Example 6 investigates the percentage fluoride retention for 82 samples of glass compositions according to the present invention; and Example 7 investigates the effect of varying melt time and temperature on the solubility and fluoride retention of the composition.

II. Preparation of Exemplary Glass Compositions

In the following examples, the solubility of the glass composition was measured in a standard solubility experiment under controlled conditions. 20 g of the cast glass was placed in a percussion mortar and given a single sharp blow with the flat face of a hammerhead. A 0.71 mm sieve was placed on a receiving bottom tray and a 1.0 mm aperture sieve was placed on top of the 0.71 mm sieve. The glass was emptied from the mortar onto the 1 mm sieve and a top pan cover was placed over the top sieve. The sieve and pan were shaken vigorously for thirty seconds and the top pan lid was then removed and the 1.0 mm sieve lifted out. The glass that was left on the top sieve only was poured back into the percussion mortar. The process was then repeated approximately three times to provide sufficient glass for the experiment.

After the third time, the whole pan and sieve assembly was placed onto a sieve vibrator and the vibrator run for 5 minutes at amplitude setting 5. The 1 mm sieve was then removed and any glass retained therein was disposed of. The 0.71 mm sieve was removed and the glass retained in this sieve was poured into a 100 ml beaker. 20 ml of acetone was added and the beaker was allowed to stand in an ultrasonic bath for seven minutes. The 100 ml beaker was then removed from the bath and the acetone was decanted off into a waste acetone bottle.

Another 20 ml of acetone was added to the beaker which was returned to the ultra sonic bath for 1 minute. This was repeated until the acetone appeared clear. Cloudy acetone indicates dust present in the glass, which will cause the solubility results to be high.

After the last acetone had been decanted, the beaker was placed in a preheated oven at 110° C. for 30 minutes. The beaker was removed from the oven and re-sieved with 1.0 mm and 0.71 mm sieves.

The solubility test involved accurately weighing approximately 1 g of washed grains and placing the grains in a numbered sinter so that the grains lie on top of the sinter. The mass of grains was recorded on a standard grain solubility record sheet noting the glass batch number and sinter number.

The numbered sinters were mounted in a water bath, set at 40° C., using the correct numbering so that the inlet and outlet tubes were attached to sinter number 1 which was clipped in the water bath in the left hand retaining clip. The number six sinter was placed in the bath at the rightmost clip. A stop clock was set for 2 hours and a pump was turned on to pass fresh deionized water over the glass samples.

After two hours the water pump and bath were turned off. The tubes were removed from the water bath, carefully decanting off the water from the top section. The tubes were clipped into the stand and approximately 20 ml of acetone was poured into each tube and allowed to drain. Once the acetone had drained from the tubes, all the tubes were placed together in a 500 ml beaker and returned to the oven for 30 minutes.

A zeroed 50 ml beaker was used to weigh the final mass of grains from each tube, while recording each mass on the standard record sheet. The final solubility is quoted in mg/g/day this being the weight loss in mg divided by the initial weight in g, divided by the time of the test in days.

III. EXAMPLE 1

FIG. 1 of the accompanying drawings illustrates the composition parameters of several exemplary glass compositions according to the present invention, labeled 1-25 respectively. The percentage fluoride retained by each composition was calculated by determining the theoretical fluoride percentage of each sample and comparing this to the analyzed level of fluoride found after the glass had been melted. The compositions were recorded as weight percentages of the elements. This was done to ensure the most accurate recording of percentage of fluoride retained. The method often used that involves recording the elements present as oxides and then recording the fluoride as a separate element is incorrect as the fluoride ions are taking the place of oxygen in the glass matrix. Assigning the fluoride ion to any particular element is also incorrect, as the actual location of the fluoride ion is unknown. The method used herein was therefore preferred and conversion to other systems is easily achieved for comparison purposes.

IV. EXAMPLE 2

The percentage of fluoride released into saliva following attachment of a glass composition of the present invention to a tooth was investigated. The batch components using compositions according to the present invention were thoroughly mixed to ensure a homogeneous melt and loaded into platinum crucibles. The crucibles were then placed in an electric melting furnace at temperatures from 600-650° C., for times of up to 60 minutes to achieve good melting. The crucibles were removed from the furnace and the glass cast onto a molding plate containing a number of circular holes of 4 mm in diameter and 6 mm in depth. The glass was rolled to force it into these cavities and when solidified the pellets were removed from the plate and transferred to an annealing oven to slowly cool and remove any residual stress.

Before use, the devices were smoothed of any rough edges with a sharp diamond burr. Three tests were carried out with human subjects and the results are reported in Tables I-III below. The device was attached to the buccal aspect of the first maxillary permanent molar because of its nearness to the opening of the parotid gland. It was felt that the salivary flow would help to distribute the fluoride to other parts of the mouth. The tooth was cleaned using a fluoride-free prophylaxis paste. After cleaning, the tooth was washed, dried and the buccal surface etched for one minute with the etch available in the composite kit (Prisma Fil-Predosed High Density Composite, The Ld. Chalk Company, Division of Dentsply International Inc., Milford, Del. 19963, U.S.A.). The glass was etched for twenty seconds. Both were washed, dried and a thin layer of a light curable adhesive from the composite kit brushed on the tooth and the glass. The glass, held by tweezers, was adapted to the tooth and cured by visible light. While temporarily held in place, a layer of light curable composite was adapted around the glass using a plastic instrument. This composite helps to retain the glass, blocks out any under cuts and makes the whole device smooth to the tongue. Once cured, the glass and composite were further smoothed with a white stone burr and a layer of fissure sealant placed on the composite and cured to give a smoother surface. Control of moisture was very important throughout this procedure. Care was taken not to cover the exposed releasing surface of the glass with any composite, bond or fissure sealant.

In this example, efforts were made to ensure that the fluoride in saliva could be accurately and repeatedly determined. The method employed was that of Taves (Separation of fluoride by rapid diffusion using hexamethyldisiloxane, Tahanta 15, 969-974, 1968), in which fluoride was diffused from the samples using hydrochloric acid saturated with hexamethyldisiloxane $(CH_3)_3SiOSi(CH_3)_3$ (hereinafter referred to as HMDS). Fluoride was collected in sodium hydroxide before its determination by a fluoride ion electrode.

For each sample of saliva, between about 1.0 and about 2.0 g (depending on the sample size) was weighed into a 60×15 mm polystyrene petri dish (Falcon Plastics Cat No. 1007, Fahrenheit Lab. Supplies, Leeds). Distilled water was added to make the final volume of 3.0 ml. Polystyrene tube caps (Falcon Plastics Cat No. 2051, Fahrenheit Lab. Supplies, Leeds.), with the rims reduced by a half, were placed in the center of each dish.

0.1 ml of 1.65M NaOH containing P-nitrophenol and phenophthalein as an indicator was added to the center of each well to ensure that the trap remained alkaline and therefore able to trap the fluoride. An alkaline trap remained pale yellow in color while an acidified trap turned pink. The lids were then sealed on the petri dishes using petroleum jelly around the-rims. Finally 1.0 ml of 6.0M HCl with HMDS was added to each dish via a small hole previously made in the lid and the hole sealed immediately with petroleum jelly and a square of sealing tissue.

The samples were placed on a rotary shaker at 200 rotations/minute and left to diffuse overnight which was usually 16 hours. The following morning the lids were pried off and a note made of any of the dishes which had not formed a vacuum since loss of the vacuum had been shown in preliminary tests to be an indicator that fluoride had been lost from the system. Each of the caps were removed and placed in an oven at 100° C. until the NaOH had become crystalline.

After drying the NaOH, the caps were placed on their test tubes and shaken with 0.34M acetic acid to dissolve the crystals and bring the pH to 5.2 for measurement by a combination fluoride ion electrode. Fluoride standards of 0.05, 0.1, 0.5, 1.0 and 5.0 µg/ml F were prepared in identically buffered solutions as the sample solutions and were used to construct a standard curve. The fluoride concentrations in the unknown diffused samples were measured from this curve using an Orion combination fluoride ion electrode and Orion 920A Ionanalyser (Orion Research Inc., Cambridge, Mass.). From the concentrations of the diffused solutions, the concentrations of fluoride in the original samples were calculated.

In all analyses, known fluoride standards and blanks were also diffused to determine the percentage diffusion that was occurring. The level of diffusion varied between 96% and 108% where a vacuum had been maintained. When known samples of fluoride solutions were diffused, the standard deviation between the recoveries was usually less than 1.0%.

Fluoride blanks were also run in this system. These included HCl-HMDS+water or NaOH alone. Fluoride was not measurable in the water or the HCl after it had been saturated with the HMDS. It appeared that the NaOH was the main contributor to the small blank of 0.002 µg/ml F.

A check was made to determine if the fluoride concentration changed if the analyses were not done on the day of collection, since it was possible that there would be too many samples to handle on some of the days when a study of salivary fluoride was being carried out and/or because laboratory facilities were not available every day. Therefore, duplicate analyses were carried out on samples which had been kept up to 7 hours at room temperature and on samples which had been stored up to 10 days at –12° C. The former was to check if study subjects could take part in collecting saliva while going about their normal work and bring the samples for analysis at the end of the collection period. The latter was to allow for the collection and storage of saliva samples when laboratory facilities were not available or for when the numbers of samples had built up beyond those which could be readily handled. No differences were found in the fluoride levels analyzed immediately, after up to 7 hours or after 10 days at –12° C.

The recovery of fluoride and reproducibility of the method were checked by using known standards and by carrying out repeat analyses on the same samples. The results of these preliminary analyses are shown in Table I below.

TABLE I

Reproductability and Recovery of Fluoride After Diffusion of Samples in HMDS-HCl

| Sample No. 3 | (ml solution) | No. of Tests | Known F[1] F | Determined F F | SD[3] | Recovery (%) |
|---|---|---|---|---|---|---|
| 1 | 1 | 4 | 0.05 | 0.045 | ±0.002 | 90 |
| 2 | 1.0 | 4 | 0.1 | 0.092 | ±0.010 | 92 |
| 3 | 0.5 | 6 | 0.5 | 0.475 | ±0.030 | 95 |
| 4 | 0.5 | 3 | 1.0 | 0.940 | ±0.010 | 94 |
| 5 | 0.2 | 2 | 5.0 | 4.900 | ±0.008 | 98 |
| 6 | Dist H$_2$O | 10 | NIL | <0.005 | ±0.000 | |
| 7 | Whole resting saliva | 6 | Unknown | 0.010 | ±0.003 | |
| 8 | Whole resting saliva | 10 | Unknown | 0.015 | ±0.005 | |

[1]F = Fluoride concentration in µg/ml
[2]Samples 1, 4, and 7 were from one standard solution or one saliva source and analyzed at the same time. 2, 5, and 6 were from known solutions or distilled H$_2$O prepared and analyzed at different times. 3 and 8 were from one solution or one saliva source analyzed at different times.
[3]SD = Standard deviation.

The results show that the recovery of fluoride by the test system was better than 90%. There was therefore an error of only 10%, which was thought to be very good, and the system was acceptable.

Table II below shows the fluoride concentration in saliva of a subject fitted with a device made from glass composition 16 of FIG. 1. A marked high increase in fluoride level in saliva was observed within the first three days. This level then settled down to a steady 0.025-0.035 µg/ml, giving on average a three-fold increase from the 0.09-0.12 µg/ml base line. The effect of the device was still clearly seen even after a year and a half in place in the subject.

TABLE II

Fluoride Concentration in µg/mL of
Saliva for Subject Fitted with Glass 16

| | | Fluoride Concentration µg/ml |
|---|---|---|
| Base line | Day 1 | 0.012 |
| | Day 2 | 0.009 |
| Treatment | Day 1 | 0.063 |
| | Day 2 | 0.039 |
| | Day 3 | 0.069 |
| | Day 4 | 0.031 |
| | Day 5 | 0.028 |
| | Day 6 | 0.037 |
| | Week 1 | 0.036 |
| | Week 2 | 0.025 |
| | Week 3 | 0.024 |
| | Month 1 | 0.030 |
| | Month 2 | 0.030 |
| | Month 3 | 0.036 |
| | Month 4 | 0.038 |
| | Month 5 | 0.034 |
| | Month 6 | 0.033 |
| | Year 1 | 0.03 |
| | Year 1.5 | 0.05 |

Table III below shows the average fluoride concentration in saliva of two subjects fitted each with a device made from composition 14 of FIG. 1. A marked high increase in fluoride level in saliva was again observed at the start but this time only for the first two days. This level then settled down to a steady 0.02-0.025 µg/ml, giving on average a two and a half fold increase from the 0.009 µg/ml base line. The device was still effective up to the four month point when it was removed.

TABLE III

Averaged Fluoride Concentration in µg/mL of
Saliva for Two Subjects Fitted with Glass 14

| | | Fluoride Concentration µg/ml. |
|---|---|---|
| Base line | Day 1 | 0.009 |
| | Day 2 | 0.009 |
| Treatment | Day 1 | 0.056 |
| | Day 2 | 0.053 |
| | Day 3 | 0.023 |
| | Day 4 | 0.024 |
| | Day 5 | 0.024 |
| | Day 6 | 0.035 |
| | Week 1 | 0.025 |
| | Week 2 | 0.022 |
| | Week 3 | 0.023 |
| | Month 1 | 0.025 |
| | Month 2 | 0.017 |
| | Month 3 | 0.022 |
| | Month 4 | 0.022 |

Table IV below shows the average fluoride concentration in saliva of four subjects fitted each with two devices made from glass composition 14 of FIG. 1. Again, the level of fluoride was high for the first three but then settled down to around the 0.035 µg/ml, a level which was a three and a half fold increase over the base line. There was also an unusually high level of fluoride recorded at weeks 1 and 2.

TABLE IV

Averaged Fluoride Concentration in µg/mL
of Saliva for Four Subjects each Fitted
with Two Devices of Glass 14

| | | Fluoride Concentration µg/ml |
|---|---|---|
| Base line | Day 1 | 0.01 |
| | Day 2 | 0.01 |
| Treatment | Day 1 | 0.043 |
| | Day 2 | 0.053 |
| | Day 3 | 0.045 |
| | Day 4 | 0.034 |
| | Day 5 | 0.041 |
| | Day 6 | 0.032 |
| | Week 1 | 0.067 |
| | Week 2 | 0.054 |
| | Week 3 | 0.033 |
| | Month 1 | 0.036 |
| | Month 2 | 0.033 |
| | Month 3 | 0.035 |
| | Month 4 | 0.033 |
| | Month 5 | 0.035 |
| | Month 6 | 0.032 |

The results clearly show that high levels of fluoride can be retained by the glass compositions of the present invention, up to about 15% F in the compositions included in FIG. 1, with acceptable levels of fluoride retention (up to about 67% in the compositions of FIG. 1).

Additionally, melting temperatures can be kept low, generally at about 650° C. or less. The glass compositions also allow fluoride to be released from the glasses for up to at least a year or more, as illustrated in Table II. Furthermnore, the level of fluoride released from the composition can be adjusted by changes in retained fluoride, glass composition and the number of devices used, as shown in FIG. 1 and Tables II to IV. Hence, the compositions of the present invention provide a glass containing fluoride for insertion into the mouth for a slow continuous release of fluoride ions, the glass being fitted either by attachment of a formal article of the glass (e.g. a glass pellet) to a tooth, or by incorporation of glass in a powder form as a dental restorative material.

V. EXAMPLE 3

An investigation was conducted to determine the salivary fluoride levels that could be achieved by increasing the percentage fluoride in three examples of glass compositions according to the present invention. The three glass devices were made with either 13.3%, 18.3% or 21.9% retained fluoride and had the following compositions:

| | Retained Fluoride: | | |
|---|---|---|---|
| | 13.3% | 18.3% | 21.9% |
| Na | 21.23 | 19.38 | 19.68 |
| P | 20.67 | 19.50 | 17.84 |
| Al | 6.76 | 8.94 | 9.90 |
| F | 19.48 | 22.12 | 25.08 |
| O | 31.86 | 30.06 | 27.49 |

The average weight of the glass devices was 82.25 mg and the quantity of fluoride in the three devices was 11.94, 15.05 and 18.01 mg F for the devices respectively. Three adult volunteers used a fluoride-free toothpaste for two weeks prior to and for the duration of the study. The glass devices were attached to the buccal surfaces of maxillary first permanent molars using an acid etch composite resin technique. Saliva samples were collected in 30 ml plastic specimen containers for two minutes as whole resting saliva, four times per day without stimulation at 0700, 1200, 1800 and 2300 hrs each day. Saliva samples were collected for two days prior to attachment of the glass devices, to establish baseline saliva fluoride levels, further saliva samples were collected for the first five days, and then weekly for one month. All saliva samples were analyzed for fluoride using a fluoride ion-specific electrode after acid diffusion according to the method of Taves (1968).

Figure 2:
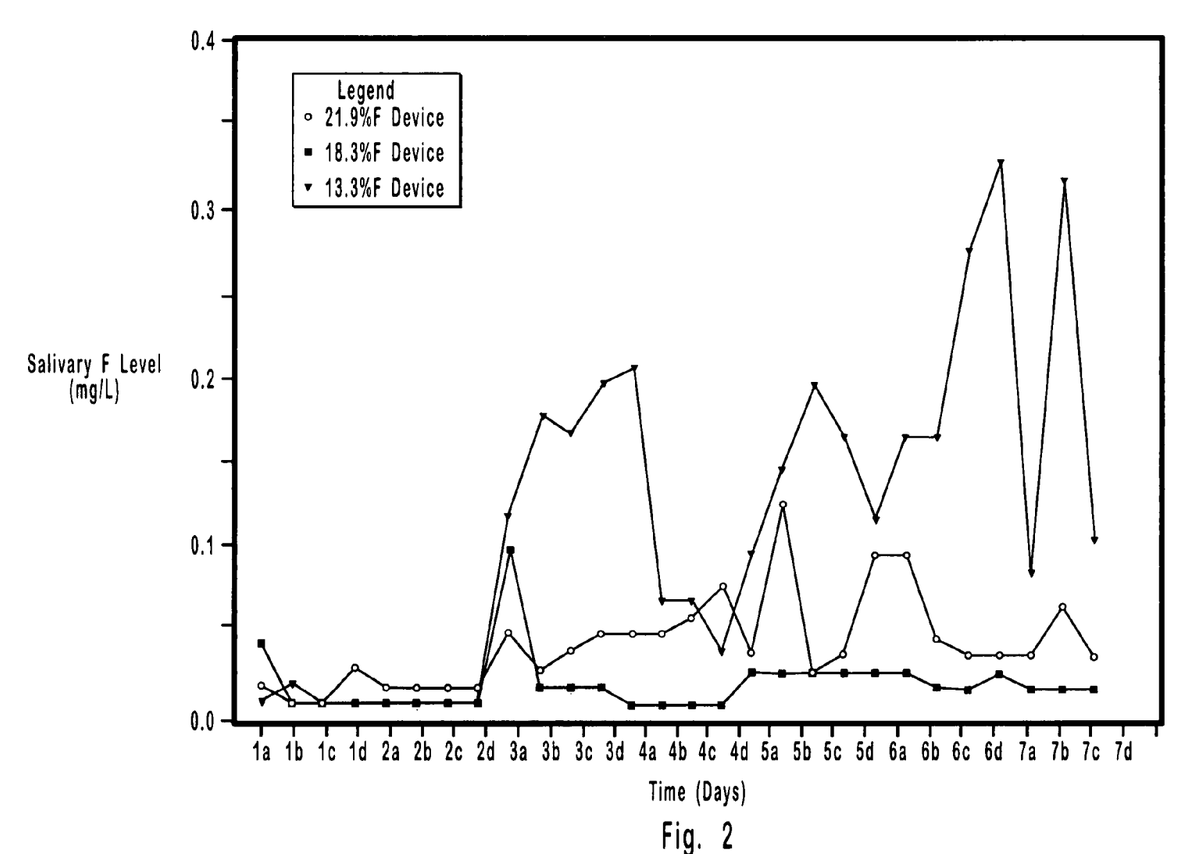
FIG. 2 is a graph illustrating the salivary fluoride levels for exemplary compositions of the present invention containing 13.3%, 18.3% and 21.9% fluoride by weight at baseline for 5 days.
Figure 3:
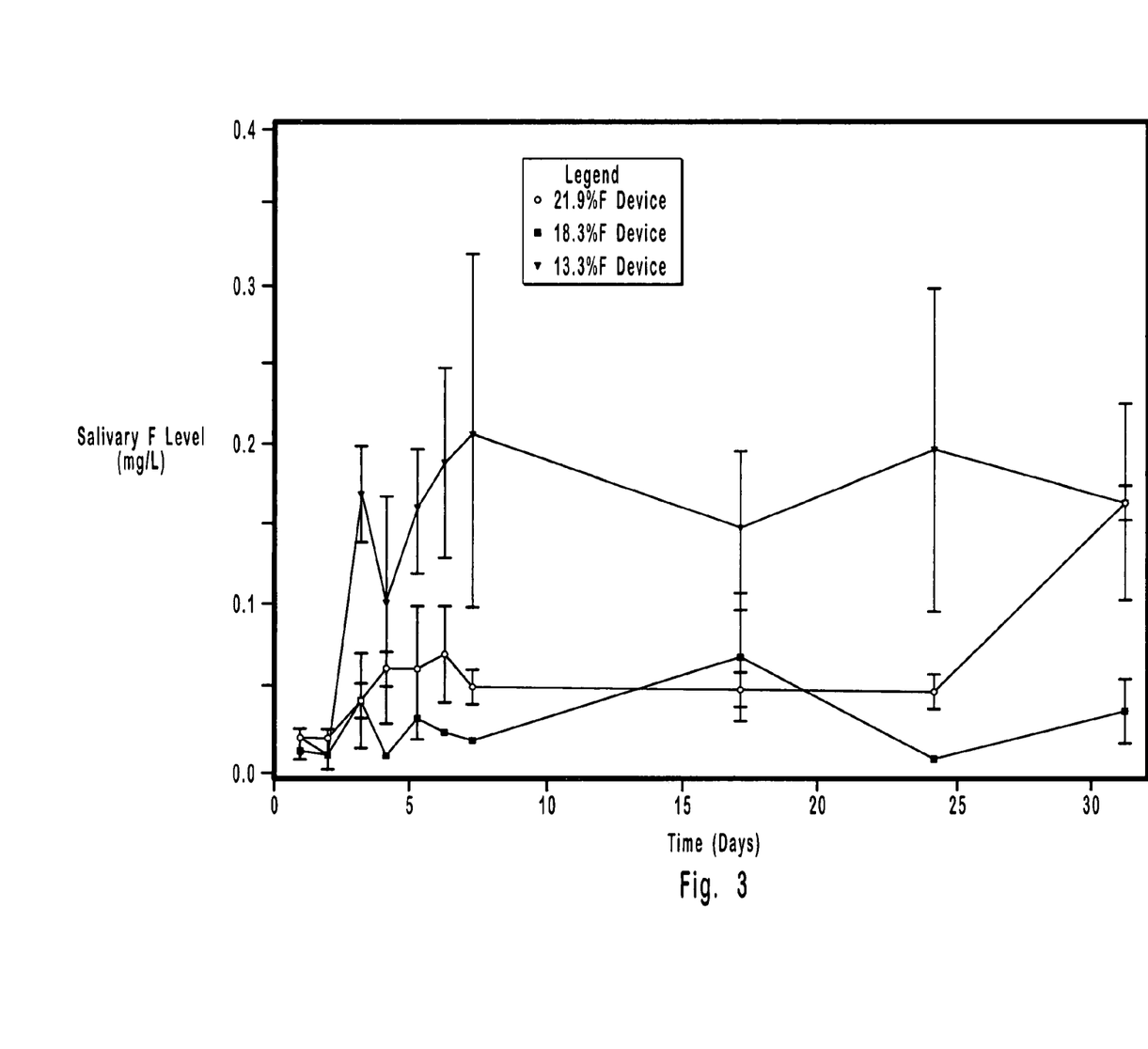
FIG. 3 is a graph illustrating the mean daily salivary fluoride levels for exemplary compositions of the present invention containing 13.3%, 18.3% and 21.9% fluoride by weight at baseline for one month.

The results of the daily and the mean daily fluoride release from the 13.3%, 18.3% and 21.9% fluoride devices for a period of one month are shown in Tables V and VI respectively. FIG. 2 illustrates the fluoride release throughout each day (i.e. four collection times per day) for baseline and the first five days after attachment of the devices. FIG. 3 illustrates the mean daily fluoride release for the three devices for the one month period. Fluoride levels were (mean, range mg/L) 13.3% =0.17, 0.04-0.37; 18.3%=0.03, 0.01-0.12; 21.9%=0.07, 0.03-0.25. Salivary fluoride levels achieved were greater for the 13.3% than the other two fluoride slow-release glass devices.

TABLE V

Daily Fluoride Levels (mg/L) for 3 Adult Volunteers with 13.3%, 18.3%, and 21.9% Fluoride Glass Devices for One Month

| Day | | 13.3% Glass (mg/L F) | 18.3% Glass (mg/L F) | 21.9% Glass (mg/L F) |
|---|---|---|---|---|
| Baseline | 1a = 0700 h | 0.01 | 0.04 | 0.02 |
| | 1b = 1200 h | 0.02 | 0.01 | 0.01 |
| | 1c = 1800 h | 0.01 | 0.01 | 0.01 |
| | 1d = 2300 h | 0.01 | 0.01 | 0.03 |
| Baseline | 2a | 0.01 | 0.01 | 0.02 |
| | 2b | 0.01 | 0.01 | 0.02 |
| | 2c | 0.01 | 0.01 | 0.02 |
| | 2d | 0.01 | 0.01 | 0.02 |
| | Means ± SD | 0.01 ± 0.003 | 0.01 ± 0.009 | 0.02 ± 0.006 |
| Day | 1a | 0.12 | 0.10 | 0.05 |
| | 1b | 0.18 | 0.02 | 0.03 |
| | 1c | 0.17 | 0.02 | 0.04 |
| | 1d | 0.20 | 0.02 | 0.05 |
| Day | 2a | 0.21 | 0.01 | 0.05 |
| | 2b | 0.07 | 0.01 | 0.05 |
| | 2c | 0.07 | 0.01 | 0.06 |
| | 2d | 0.04 | 0.01 | 0.08 |
| Day | 3a | 0.10 | 0.03 | 0.04 |
| | 3b | 0.15 | 0.03 | 0.13 |
| | 3c | 0.20 | 0.03 | 0.03 |
| | 3d | 0.17 | 0.03 | 0.04 |
| Day | 4a | 0.12 | 0.03 | 0.10 |
| | 4b | 0.17 | 0.03 | 0.10 |
| | 4c | 0.17 | 0.02 | 0.05 |
| | 4d | 0.28 | 0.02 | 0.04 |
| Day | 5a | 0.33 | 0.03 | 0.04 |
| | 5b | 0.09 | 0.02 | 0.04 |
| | 5c | 0.32 | 0.02 | 0.07 |
| | 5d | 0.11 | 0.02 | 0.04 |
| Week | 2a | 0.17 | 0.08 | 0.05 |
| | 2b | 0.075 | 0.12 | 0.04 |
| | 2c | 0.15 | 0.04 | 0.04 |
| | 2d | 0.21 | 0.03 | 0.07 |
| Week | 3a | 0.375 | 0.01 | 0.04 |
| | 3b | 0.10 | 0.01 | 0.04 |
| | 3c | 0.17 | 0.01 | 0.05 |
| | 3d | 0.17 | 0.01 | 0.06 |
| Week | 4a | 0.17 | 0.08 | 0.20 |
| | 4b | 0.17 | 0.04 | 0.10 |
| | 4c | 0.15 | 0.02 | 0.25 |
| | 4d | 0.19 | 0.02 | 0.12 |
| | Means ± SD | 0.17 ± 0.07 | 0.03 ± 0.026 | 0.07 ± 0.05 |

TABLE VI

Mean (±SD) Daily Fluoride Levels (mg/L) for 3 Adult volunteers with 13.3%, 18.3% and 21.9% Glass Device for One Month

| Day | 13.3% Glass (mg/L F) | 18.3% Glass (mg/L F) | 21.9% Glass (mg/L F) |
|---|---|---|---|
| Baseline 1 | 0.01 | 0.02 | 0.02 |
| Baseline 2 | 0.01 | 0.01 | 0.02 |
| Mean ± SD | 0.01 ± 0.003 | 0.01 ± 0.009 | 0.02 ± 0.006 |
| Day 1 | 0.17 ± 0.03 | 0.04 ± 0.03 | 0.04 ± 0.01 |
| Day 2 | 0.10 ± 0.07 | 0.01 ± 0.01 | 0.06 ± 0.01 |
| Day 3 | 0.16 ± 0.04 | 0.03 ± 0.01 | 0.06 ± 0.04 |
| Day 4 | 0.19 ± 0.06 | 0.03 ± 0.01 | 0.07 ± 0.03 |
| Day 5 | 0.21 ± 0.11 | 0.02 ± 0.01 | 0.05 ± 0.01 |
| Week 2 | 0.15 ± 0.05 | 0.07 ± 0.04 | 0.05 ± 0.01 |
| Week 3 | 0.20 ± 0.10 | 0.01 ± 0.01 | 0.05 ± 0.01 |
| Week 4 | 0.17 ± 0.01 | 0.04 ± 0.02 | 0.17 ± 0.06 |
| Mean ± SD | 0.17 ± 0.07 | 0.03 ± 0.026 | 0.07 ± 0.05 |

Pooled human unstimulated saliva was collected from normal adult volunteers as whole resting saliva and divided into 15 aliquots of 3ml in plastic tubes. The saliva samples were used for the study immediately following the collection period. Five samples of each of the three glass devices containing 13.3%, 18.3%, and 21.9% fluoride were placed into each of the plastic tubes containing the aliquot of the pooled saliva. These were placed on a Ika-Vibrax VXR rotary shaker at 200 rotations per minute and left for two hours. 1 ml aliquots were taken from each tube in duplicate and analyzed for fluoride together with duplicate samples of the pooled saliva using a fluoride ion-specific electrode after acid diffusion according to the method of Taves (1968).

The results of the in vitro salivary fluoride levels of the 13.3%; 18.3%, and 21.9% F devices shaken for two hours in pooled human saliva is shown in Table VII. The level of fluoride release was again greater for the 13.3% device.

TABLE VII

In Vitro Salivary Fluoride Levels (mg/L) of 13.3%, 18.3% and 21.9% Fluoride Glass Devices Shaken for 2 Hours with Pooled Adult Human Saliva

| Pooled Saliva (mg/L F) | 13.3% Glass (mg/L F) | 18.3% Glass (mg/L F) | 21.9% Glass (mg/L F) |
|---|---|---|---|
| 0.06 | 2.21 | 1.52 | 1.02 |
| 0.06 | 2.07 | 1.41 | 1.05 |
| 0.06 | 2.19 | 1.50 | 0.99 |
| 0.06 | 2.20 | 1.55 | 0.99 |
| 0.06 | 2.22 | 1.48 | 1.01 |
| Mean ± SD | Mean ± SD | Mean ± SD | Mean ± SD |
| 0.06 ± 0.00 | 2.18 ± 0.05 | 1.49 ± 0.05 | 1.01 ± 0.02 |

The results of the study of fluoride release from the slow-release devices containing increasing amounts of fluoride gave surprising results. Salivary fluoride levels achieved were surprisingly greater for the 13.3% device than the other two higher percentage fluoride glasses. It had been expected that the higher fluoride concentration glass devices would yield the highest salivary fluoride levels. The greater fluoride release from the 13.3% device was confirmed from the in vitro study. A post-study review showed that due to manufacturing considerations the 18.3% and 21.9% devices contained a mixture of aluminum fluoride and sodium fluoride, whereas the 13.3% device contained sodium fluoride alone. Aluminum reacts with fluoride strongly to form aluminum fluoride, which is much less soluble than other forms of fluoride. Therefore, the fluoride glass devices containing aluminum fluoride were in comparison to the sodium fluoride glass device, relatively insoluble with respect to fluoride release. Therefore, fluoride was more available from the 13.3% fluoride device which was felt to be better as a slow-releasing device for the future studies.

VI. EXAMPLE 4

It was felt necessary to determine which tooth sites were most appropriate for attachment of the devices and for fluoride release. Volunteers used the same fluoride-free toothpaste for two weeks prior to and for the duration of the study. Four adult volunteers or each had fluoride glass devices attached to the buccal surfaces of their maxillary right first permanent molar teeth. Another four adult volunteers had fluoride glass devices attached bilaterally to the buccal surfaces of their maxillary right and left first permanent molar teeth. Finally, four adult volunteers had fluoride glass devices attached to the buccal surfaces of their mandibular right first permanent molar teeth. Finally, four adult volunteers had fluoride glass devices attached to the lingual surfaces of their mandibular right and left permanent canine teeth. All of the fluoride glass devices contained 13.3% fluoride, and were attached to the tooth sites using the acid etch composite technique.

Table VIII shows the salivary fluoride levels of the volunteers at baseline and at one day, one week and two weeks post-insertion of the glass devices. The mean salivary fluoride levels were 0.01-0.02 mg/L F at baseline and 0.17-0.18 mg/L F post insertion of the F devices.

TABLE VIII

Mean Salivary Fluoride Levels of Adult Human Volunteers Whilst Wearing Lower Appliances with 13.3% Fluoride Glass Devices Attached

| Day | Volunteer 1 (mg/L F) | Volunteer 2 (mg/L F) | Volunteer 3 (mg/L F) | Volunteer 4 (mg/L F) |
|---|---|---|---|---|
| Baseline | 0.01 | 0.01 | 0.02 | 0.01 |
| Day 1 | 0.18 | 0.17 | 0.18 | 0.18 |
| Week 1 | 0.17 | 0.17 | 0.18 | 0.18 |
| Week 2 | 0.17 | 0.18 | 0.18 | 0.17 |
| Mean(±SD) | 0.17(±0.01) | 0.17(±0.01) | 0.18(±0.01) | 0.18(±0.02) |

The above findings suggest that fluoride is distributed around the mouth from these devices and does not remain site specific.

VII. EXAMPLE 5

Samples of the glass composition in powdered form were provided, the samples were of two grain sizes as follows:
1) <about 38 microns
2) <about 106 microns and of three relative solubilities as follows:
1) about 1
2) about 10
3) about 100

The three samples had the following compositions:

| | Relative Solubility: | | |
|---|---|---|---|
| | 1 | 10 | 100 |
| Na | 18.23 | 21.23 | 25.92 |
| P | 20.85 | 20.67 | 20.39 |
| Al | 8.41 | 6.76 | 4.18 |
| F | 20.38 | 19.48 | 18.08 |
| O | 32.13 | 31.86 | 31.43 |

0.1 g. of each of the powdered fluoride glass samples was mixed with 1.0 g of Aurafill light curing composite restorative material (Gray shade, Johnson & Johnson) and placed in a 5 mm diameter plastic mold and light cured for 60 seconds to provide fluoride glass-composite pellets. Duplicate pellets of each of the powdered glass samples were prepared with the composite material and duplicate pellets of composite material alone were also prepared to act as controls. A total of 14 pellets were prepared. Each pellet was weighed (mean weight 0.28±0.01 S.D.) and the pellets were placed in plastic tubes (Falcon Code 2051) with 3 ml of distilled water and left for 24 hours. One ml aliquots were analyzed for fluoride in duplicate after acid diffusion according to the method of Taves (1968). The pellets were then replaced in their plastic tubes containing fresh 3 ml aliquots of distilled water. One ml aliquots were analyzed for fluoride daily (except at weekends) for a period of one month.

Figure 4:
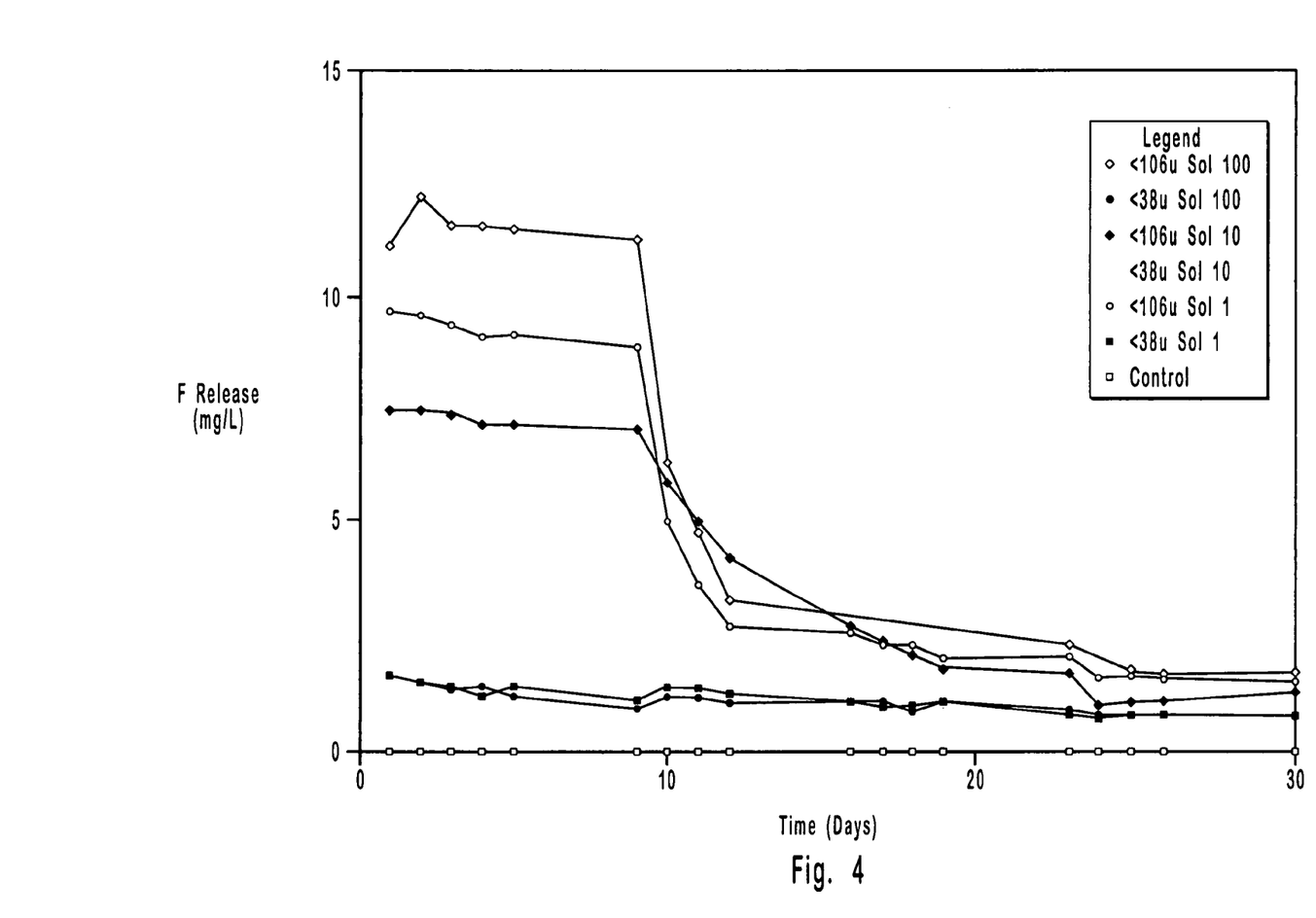
FIG. 4 is a graph illustrating the mean daily fluoride release over one month for powdered fluoride glass composite pellets according to one embodiment of the present invention.

The in vitro results of the daily fluoride release for a period of one month of the powdered forms of the fluoride glass, of two grain sizes (<38 microns and <106 microns) and of three relative solubilities (1, 10 and 100), when mixed with composite material are shown in Table IX below and illustrated in FIG. 4. Table X below shows the in vitro results when the powdered fluoride glass composite mixes were left undisturbed for a period of four weeks. Fluoride was released at mean levels ranging from 1.5-12.2 mg/L daily at commencement, and 0.8-1.8 mg/L at the end of the study. The <38 micron grain size with a relative solubility of 1 showed consistent fluoride release of 0.7-1.5 mg/L daily throughout the study.

TABLE IX

| | Control (mg/LF) | <38 μm Sol 1 (mg/LF) | <106 μm Sol 1 (mg/LF) | <38 μm Sol 10 (mg/LF) | <106 μm Sol 10 (mg/LF) | <38 μm Sol 100 (mg/LF) | <106 μm Sol 100 (mg/LF) |
|---|---|---|---|---|---|---|---|
| Day 1 | 0.0 | 1.5 ± 0.0 | 1.5 ± 0.1 | 6.6 ± 0.2 | 7.5 ± 0.3 | 9.7 ± 0.2 | 12.2 ± 0.3 |
| Day 2 | 0.0 | 1.4 ± 0.2 | 1.4 ± 0.1 | 6.5 ± 0.1 | 7.5 ± 0.2 | 9.6 ± 0.1 | 12.2 ± 0.2 |
| Day 3 | 0.0 | 1.3 ± 0.1 | 1.3 ± 0.1 | 6.5 ± 0.2 | 7.4 ± 0.2 | 9.4 ± 0.3 | 11.6 ± 0.3 |
| Day 4 | 0.0 | 1.2 ± 0.1 | 1.3 ± 0.1 | 6.2 ± 0.1 | 7.2 ± 0.1 | 9.1 ± 0.2 | 11.6 ± 0.2 |
| Day 5 | 0.0 | 1.3 ± 0.2 | 1.2 ± 0.1 | 6.3 ± 0.1 | 7.2 ± 0.2 | 9.2 ± 0.1 | 11.5 ± 0.2 |
| Day 8* | 0.0 | 2.6 ± 0.1 | 2.4 ± 0.1 | 10.4 ± 0.2 | 13.1 ± 0.1 | 15.6 ± 0.2 | 18.3 ± 0.2 |

TABLE IX-continued

|  | Control (mg/LF) | <38 μm Sol 1 (mg/LF) | <106 μm Sol 1 (mg/LF) | <38 μm Sol 10 (mg/LF) | <106 μm Sol 10 (mg/LF) | <38 μm Sol 100 (mg/LF) | <106 μm Sol 100 (mg/LF) |
|---|---|---|---|---|---|---|---|
| Day 9 | 0.0 | 1.1 ± 0.0 | 0.9 ± 0.0 | 5.3 ± 0.3 | 7.0 ± 0.1 | 8.9 ± 0.3 | 11.3 ± 0.7 |
| Day 10 | 0.0 | 1.3 ± 0.1 | 1.2 ± 0.1 | 4.0 ± 0.0 | 5.9 ± 0.4 | 5.0 ± 0.6 | 6.4 ± 0.3 |
| Day 11 | 0.0 | 1.3 ± 0.1 | 1.2 ± 0.1 | 2.8 ± 0.1 | 5.0 ± 0.6 | 3.6 ± 0.1 | 4.8 ± 0.5 |
| Day 12 | 0.0 | 1.2 ± 0.1 | 1.1 ± 0.0 | 2.0 ± 0.1 | 4.2 ± 0.4 | 2.7 ± 0.1 | 3.3 ± 0.1 |
| Day 15* | 0.0 | 2.3 ± 0.2 | 2.2 ± 0.1 | 2.8 ± 0.1 | 7.2 ± 0.6 | 6.8 ± 0.0 | 7.1 ± 0.1 |
| Day 16 | 0.0 | 1.1 ± 0.1 | 1.1 ± 0.0 | 0.9 ± 0.0 | 2.7 ± 0.2 | 2.6 ± 0.1 | 2.7 ± 0.0 |
| Day 17 | 0.0 | 1.0 ± 0.1 | 1.1 ± 0.1 | 0.7 ± 0.0 | 2.4 ± 0.1 | 2.3 ± 0.1 | 2.4 ± 0.1 |
| Day 18 | 0.0 | 1.0 ± 0.1 | 0.9 ± 0.0 | 0.6 ± 0.1 | 2.1 ± 0.2 | 2.3 ± 0.1 | 2.3 ± 0.3 |
| Day 19 | 0.0 | 1.1 ± 0.1 | 1.1 ± 0.1 | 0.6 ± 0.0 | 1.8 ± 0.2 | 2.0 ± 0.1 | 2.0 ± 0.1 |
| Day 22* | 0.0 | 1.6 ± 0.2 | 1.7 ± 0.1 | 1.4 ± 0.1 | 2.8 ± 0.3 | 4.5 ± 0.0 | 4.5 ± 0.1 |
| Day 23 | 0.0 | 0.8 ± 0.1 | 0.9 ± 0.0 | 0.8 ± 0.0 | 1.7 ± 0.0 | 2.1 ± 0.1 | 2.4 ± 0.3 |
| Day 24 | 0.0 | 0.7 ± 0.1 | 0.8 ± 0.1 | 0.5 ± 0.0 | 1.0 ± 0.2 | 1.6 ± 0.1 | 1.6 ± 0.1 |
| Day 25 | 0.0 | 0.8 ± 0.1 | 0.8 ± 0.1 | 0.7 ± 0.1 | 1.1 ± 0.1 | 1.7 ± 0.2 | 1.8 ± 0.1 |
| Day 26 | 0.0 | 0.8 ± 0.1 | 0.8 ± 0.1 | 0.7 ± 0.1 | 1.1 ± 0.1 | 1.6 ± 0.1 | 1.7 ± 0.2 |
| Day 29* | 0.0 | 1.2 ± 0.1 | 1.3 ± 0.1 | 1.0 ± 0.1 | 1.9 ± 0.1 | 3.1 ± 0.1 | 3.3 ± 0.1 |
| Day 30 | 0.0 | 0.8 ± 0.1 | 0.8 ± 0.1 | 0.6 ± 0.0 | 1.3 ± 0.1 | 1.6 ± 0.1 | 1.8 ± 0.1 |

*Indicates when pellets were left over the weekend, i.e., for longer than one day.

Powdered F glass samples:

<38 microns, Relative Solubility = 1
<106 microns, Relative Solubility = 1
<38 microns, Relative Solubility = 10
<106 microns, Relative Solubility = 10
<38 microns, Relative Solubility = 100
<106 microns, Relative Solubility = 100

0.1 g of each of the powdered F glass samples was mixed with 1.0 g of Aurafill® composite material.
Mean Weight (±SD) of Pellets=0.28 g (±0.01)

TABLE X

In Vitro Mean Fluoride Levels (mg/L) for Powdered Glass-Composite Pellets Left Undisturbed for Four Weeks

| F Glass-Composite Mixture | | Mean (±SD) F Release (mg/L F) |
|---|---|---|
| Control | | 0.0 ± 0.0 |
| 1) | <38 microns, Relative Solubility = 1 | 12.9 ± 2.6 |
| 2) | <106 microns, Relative Solubility = 1 | 9.0 ± 1.1 |
| 3) | <38 microns, Relative Solubility = 10 | 38.0 ± 1.6 |
| 4) | <106 microns, Relative Solubility = 10 | 44.3 ± 3.8 |
| 5) | <38 microns, Relative Solubility = 100 | >100.0 |
| 6) | <106 microns, Relative Solubility = 100 | >100.0 |

0.1 g of each of the powdered F glass samples was mixed with 1.0 g of Aurafill® composite material.
Mean Weight (±SD) of Pellets=0.28 g (±0.01)

The powdered form of the fluoride glass having <about 38 micron grain size with a relative solubility of 1 has great potential for incorporation into a number of dental materials, with preventive actions in a number of dental disciplines. It may be added to dental restorative materials for routine conservation, with the aim of preventing caries around the margins of restorations. In addition, it will provide a source of long term intra-oral fluoride for prevention of new carious lesions. Incorporation within fissure sealants may well provide longer term fluoride release than the seven day burst effect reported by Cooley et al (1990). In orthodontics, it could be added to composite bonding materials to cement bands and brackets. Addition to orthodontic bonding materials would be of great value in prevention of the widespread enamel demineralization that is observed around orthodontic bands and brackets (Shannon & West, 1979; Chadwick, 1994; Chadwick & Gordon, 1995). Again the use in orthodontics would be of considerable benefit as the majority of malocclusions requiring fixed appliance therapy are of two years duration. Hence, if one of the glass devices could be attached to a band or bracket or the fluoride glass incorporated within the bonding material, then protection for the duration of the orthodontic treatment would be ensured. It may also be possible to incorporate the fluoride glass powder within acrylic resin for construction of removable orthodontic appliances. Boyd (1993) compared the effectiveness of a 1100 ppm fluoride toothpaste used alone, or together with a 0.05% sodium fluoride daily rinse or a 0.4% stannous fluoride gel applied twice daily, in controlling the decalcification that accompanies orthodontic treatment. Boyd's results indicated that twice daily use of the fluoride toothpaste and either a once-daily fluoride rinse or a twice-daily fluoride gel provided additional protection against decalcification beyond that achieved with fluoride toothpaste alone. Similarly, in prosthetic dentistry, the use of the fluoride glass powder in acrylic will have potential for fluoride release around abutment teeth. In periodontology, the application of this form of fluoride within a resin varnish may be of benefit in the treatment of exposed sensitive root dentine. A role in oral surgery may also be possible, for example the prior coating of implants with this material. Patients suffering from xerostomia from a variety of causes are at greater caries-risk, and therefore, these devices would have an important caries-preventive role for this group of patients. Root dentine caries is a common occurrence in the elderly, and these devices would also have an important preventive role.

VIII. EXAMPLE 6

Further glass compositions according to the present invention were studied for their composition parameters. The results are shown in FIG. 5 of the accompanying drawings. The glass compositions are labeled 1-82 respectively and are shown in order of solubility. The glass composition chosen for a particular application will depend upon the duration and amount of fluoride release required. Glass compositions experiencing devitrification or phase separation (see FIG. 5, indicated by 1-5, with 5 having the most extensive devitrification or phase separation) do not form true glasses.

Table XI below shows the overall range of compositions studied, the compositions that formed good glasses, the compositions that provided the preferred solubility and the range that provide both good glass and the preferred solubility.

As described in the examples above, the glass composition may comprise a pellet such as described in conjunction with Example 2, any other shape or configuration placeable within a patient's mouth, or a powder. The powdered form of the fluoride glass has great potential for incorporation into a number of dental materials. It may be added to dental materials including fissure sealants, orthodontic composite bonding materials or resins from which orthodontic appli-

TABLE XI

Ranges

| | OVERALL RANGE OF COMPOSITIONS | | GOOD GLASS | | PREFERRED | | GOOD GLASS | |
|---|---|---|---|---|---|---|---|---|
| | MIN. | MAX. | MIN. | MAX. | MIN. | MAX. | MIN. | MAX. |
| Na | 6.81 | 24.25 | 11.86 | 24.25 | 6.81 | 23.62 | 11.86 | 22.6 |
| P | 17.09 | 22.37 | 18.08 | 22.37 | 17.09 | 22.37 | 18.08 | 22.37 |
| Al | 3.39 | 8.87 | 4.31 | 8.87 | 4.31 | 7.48 | 4.31 | 7.48 |
| F | 16.22 | 24.5 | 16.22 | 24.1 | 16.27 | 22.87 | 16.27 | 22.87 |
| O | 26.43 | 34.48 | 27.87 | 34.48 | 26.43 | 34.48 | 27.87 | 34.48 |
| K | 0 | 21.36 | 0 | 13.87 | 0 | 21.36 | 0 | 13.87 |
| Ca | 0 | 5.75 | 0 | 5.75 | 0 | 5.75 | 0 | 5.75 |
| Mg | 0 | 5.6 | 0 | 2.61 | 0 | 2.61 | 0 | 2.61 |
| Na + K | 17.73 | 28.17 | 19.08 | 25.78 | 19.08 | 28.17 | 19.08 | 25.73 |
| F Retention | 44.4 | 65.54 | 44.4 | 65.54 | 47.74 | 65.54 | 47.94 | 65.54 |
| Solubility | 45 | 10429 | 45 | 10429 | 100 | 1006 | 100 | 1006 |
| F Analyzed | 7.8 | 14.2 | 7.8 | 14.2 | 7.8 | 13.5 | 7.8 | 13.5 |

IX. EXAMPLE 7

Samples 1, 13 and 31 of Example 6 were investigated to determine the effect of varying melt time and temperature on the solubility and fluoride retention of the composition. Table XII below illustrates the results of the investigations:

ances (e.g. brackets) may be made. Similarly, the fluoride glass powder may be incorporated with acrylic resins for dental prosthetics. In periodontology, the application of this form of fluoride within a resin varnish may be used in the treatment of exposed sensitive root dentine. A role in oral

TABLE XII

Effect of Varying Melt Time and Temperature

| Code | Na | P | Al | F | O | K | Ca | Mg | TOT | Na + K | F Anal. | Sol. | Ret. | Melt Temp. | Melt Time |
|---|---|---|---|---|---|---|---|---|---|---|---|---|---|---|---|
| 1 | 21.23 | 20.67 | 6.76 | 19.48 | 31.86 | 0 | 0 | 0 | 100 | 21.23 | 8.9 | 115 | 45.7 | 650 | 45 |
| 1 | 21.23 | 20.67 | 6.76 | 19.48 | 31.86 | 0 | 0 | 0 | 100 | 21.23 | 8.1 | 116 | 41.6 | 650 | 90 |
| 1 | 21.23 | 20.67 | 6.76 | 19.48 | 31.86 | 0 | 0 | 0 | 100 | 21.23 | 9.6 | 98 | 49.3 | 700 | 45 |
| 1 | 21.23 | 20.67 | 6.76 | 19.48 | 31.86 | 0 | 0 | 0 | 100 | 21.23 | 8.1 | 94 | 41.9 | 700 | 90 |
| 1 | 21.23 | 20.67 | 6.76 | 19.48 | 31.86 | 0 | 0 | 0 | 100 | 21.23 | 9.6 | 95 | 49.3 | 750 | 45 |
| 1 | 21.23 | 20.67 | 6.76 | 19.48 | 31.86 | 0 | 0 | 0 | 100 | 21.23 | 7.4 | 77 | 38.0 | 750 | 90 |
| 13 | 22.72 | 20.31 | 6.11 | 19.56 | 31.3 | 0 | 0 | 0 | 100 | 22.72 | 9.3 | 1209 | 47.5 | 650 | 45 |
| 13 | 22.72 | 20.31 | 6.11 | 19.56 | 31.3 | 0 | 0 | 0 | 100 | 22.72 | 8.4 | 984 | 42.9 | 650 | 90 |
| 13 | 22.72 | 20.31 | 6.11 | 19.56 | 31.3 | 0 | 0 | 0 | 100 | 22.72 | 10 | 1134 | 51.1 | 700 | 45 |
| 13 | 22.72 | 20.31 | 6.11 | 19.56 | 31.3 | 0 | 0 | 0 | 100 | 22.72 | 8.1 | 892 | 41.4 | 700 | 90 |
| 13 | 22.72 | 20.31 | 6.11 | 19.56 | 31.3 | 0 | 0 | 0 | 100 | 22.72 | 8.7 | 1180 | 44.5 | 750 | 45 |
| 13 | 22.72 | 20.31 | 6.11 | 19.56 | 31.3 | 0 | 0 | 0 | 100 | 22.72 | 7.8 | 822 | 39.9 | 750 | 90 |
| 31 | 19.27 | 19.95 | 4.79 | 18.74 | 30.75 | 4.49 | 1.14 | 0.87 | 100 | 23.76 | 9.2 | 570 | 49.1 | 650 | 45 |
| 31 | 19.27 | 19.95 | 4.79 | 18.74 | 30.75 | 4.49 | 1.14 | 0.87 | 100 | 23.76 | 10.1 | 440 | 53.9 | 650 | 90 |
| 31 | 19.27 | 19.95 | 4.79 | 18.74 | 30.75 | 4.49 | 1.14 | 0.87 | 100 | 23.76 | 10 | 508 | 53.4 | 700 | 45 |
| 31 | 19.27 | 19.95 | 4.79 | 18.74 | 30.75 | 4.49 | 1.14 | 0.87 | 100 | 23.76 | 9.2 | 379 | 49.1 | 700 | 90 |
| 31 | 19.27 | 19.95 | 4.79 | 18.74 | 30.75 | 4.49 | 1.14 | 0.87 | 100 | 23.76 | 10.2 | 452 | 54.4 | 750 | 45 |
| 31 | 19.27 | 19.95 | 4.79 | 18.74 | 30.75 | 4.49 | 1.14 | 0.87 | 100 | 23.76 | 8.9 | 352 | 47.5 | 750 | 90 |

Exemplary Methods of Use

As mentioned above, the inventive method involves treating sensitive teeth by attaching a fluoride releasing glass composition to a person's tooth, and then allowing fluoride to be slowly released over time in order to reduce chronic and/or acute tooth sensitivity.

surgery may also be possible, for example by coating or otherwise incorporating the glass composition within implants.

In order to test the effect of fluoride releasing glass on dentine sensitivity, slow release fluoride devices (SRFDs) containing 17.4% fluoride were attached to the buccal surfaces of upper permanent molar teeth using an acid etch composite technique in 10 (5 male and 5 female) healthy adults suffering from primary dentine sensitivity. The degree of dentine sensitivity was assessed on a patient basis at baseline, 2 weeks, 1, 3, and 6 months by the subjects using a four point analogue scale as: severe, moderate, mild, or not at all. Subjects used a fluoride free toothpaste for the duration of the study. Salivary fluoride release was determined at baseline and 6 months using a fluoride ion-specific electrode and TISAB buffer. Whole unstimulated mixed saliva was collected by pooling in the mouth for 2 minutes prior to drooling into plastic containers. This was performed at least 3 hours after tooth brushing. The saliva samples were either analyzed within 12 hours or frozen at −12° C. until they were analyzed. The retention of the devices and their effects on the intra-oral tissues were also assessed. Any possible effects on soft tissues (buccal mucosa, gingival, etc.) were also recorded. Gingivitis was assessed at baseline and 6 months according to the Gingival Index of Loe, 1967.

Plaque was scored at the same time using the Plaque Index of Loe, 1967. Ulceration, irritation and erythema of all intra-oral soft tissues were also checked at baseline and at 6 months. All of the devices remained intact for the duration of the study and there were no adverse effects reported or observed on the intra-oral soft tissues. Mean salivary fluoride levels at baseline were 0.02±0.01 mg/L and 0.16±0.02 mg/L at 6 months (p<0.01). Dentine sensitivity was graded as severe (7 subjects), moderate (2 subjects) and mild (1 subject) at baseline. All 10 subjects reported complete alleviation of their sensitivity by 2 weeks and for the remainder of the study period. The mean plaque index was 1.78±0.20 at baseline and 1.94±0.33 at 6 months and the mean gingival index was 0.55±0.13 at baseline and 0.65±0.15 at 6 months (non significant difference using t-test). These results are recorded in Table XIII.

TABLE XIII

|  | Baseline | 2 weeks | 1 month | 3 months | 6 months |
|---|---|---|---|---|---|
| Sensitivity: |  |  |  |  |  |
| Not at all | 0 | 10 | 10 | 10 | 10 |
| Mild | 1 | 0 | 0 | 0 | 0 |
| Moderate | 2 | 0 | 0 | 0 | 0 |
| Severe | 7 | 0 | 0 | 0 | 0 |
| Mean Salivary Fluoride (mg/L) | 0.02 ± 0.01 |  |  |  | 0.16 ± 0.02 |
| Mean Plaque Index | 1.78 ± 0.20 |  |  |  | 1.94 ± 0.33 |
| Mean Gingival Index | 0.55 ± 0.13 |  |  |  | 0.65 ± 0.15 |

Slow-release fluoride devices consistently raise intra-oral salivary fluoride levels for periods up to 2 years or more, and now also appear to completely alleviate the symptoms of dentine sensitivity within two weeks, while maintaining the benefit for up to six months or more in adults. All 10 of the adult subjects reported complete alleviation of their dentine sensitivity. There were no adverse events reported or observed. There was a slight tendency for an increase in plaque and gingival indices, but this was non-significant.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A method of treating sensitive teeth comprising:
    attaching a fluoride releasing glass composition to a person's tooth,
        wherein the glass composition is formed by combining and melting a phosphorus oxide and at least one of sodium, potassium, lithium or aluminum in oxide and/or fluoride form, the glass composition optionally comprising silicon in an amount up to about 5% by weight,
        wherein the glass composition has the general empirical formula given below, expressed in approximate weight percent of each element:
        phosphorus: 16-24
        fluorine: 5-30
        oxygen: 20-40; and
    allowing a therapeutically effective amount of fluoride to be slowly released over time as the glass composition is exposed to saliva within the person's mouth in order for the fluoride to contact tooth surfaces and thereby reduce chronic and/or acute tooth sensitivity.

2. The method as recited in claim 1, wherein the fluoride releasing glass composition includes at least one of sodium, potassium, lithium, or aluminum in an amount up to a total of about 40 weight percent and optionally, up to about 5 weight percent of boron and/or silicon.

3. The method as recited in claim 2, wherein fluorides and/or oxides of glass modifiers are included in the composition.

4. The method as recited in claim 3, wherein the fluorine is included in compounds selected from the group consisting of aluminum fluoride, sodium hydrogen fluoride, sodium fluoride, calcium fluoride, magnesium fluoride, and potassium fluoride.

5. The method as recited in claim 2, further comprising one or more other glass modifiers.

6. The method as recited in claim 5, wherein the other glass modifiers are calcium, magnesium, and/or zinc.

7. The method as recited in claim 5, wherein the other glass modifiers are included in an amount up to about 10 weight percent.

8. The method as recited in claim 2, wherein the composition includes a combined weight percent of at least about 16 percent of sodium and potassium.

9. The method as recited in claim 2, wherein the composition includes a combined weight percent of between about 19 and about 26 percent of sodium and potassium.

10. The method as recited in claim 2, wherein aluminum is included in an amount of at least about 3 weight percent.

11. The method as recited in claim 2, wherein aluminum is included in an amount of between about 4 and about 10 weight percent.

12. The method as recited in claim 2, wherein at least about 25 weight percent oxygen is included in the composition.

13. The method as recited in claim 2, wherein between about 25 and about 35 weight percent oxygen is included in the composition.

14. The method as recited in claim 2, wherein phosphorus is included in an amount of about 17 to about 23 weight percent.

15. The method as recited in claim 2, wherein at least about 12 weight percent of fluoride is included in the composition.

16. The method as recited in claim 2, wherein between about 15 and about 25 weight percent fluorine is included in the composition.

17. The method as recited in claim 2, wherein the composition provides a fluoride retention of at least about 45 percent at a melting temperature of no more than about 650° C. over 45 minutes.

18. The method as recited in claim 2, wherein the composition has a solubility in the range of about 5 to about 10,000.

19. The method as recited in claim 2, wherein the composition has a solubility in the range of about 5 to about 100.

20. The method as recited in claim 2, wherein the composition is provided in powder form.

21. The method as recited in claim 20, wherein the powder form of the glass composition comprises powder grains having a grain size of less than about 38 microns.

22. The method as recited in claim 20, wherein the powder form of the glass composition comprises powder grains having a grain size of less than about 106 microns.

23. The method as recited in claim 20, wherein the powdered composition is incorporated in one or more dental materials.

24. The method as recited in claim 23, wherein the dental material is selected from the group consisting of a dental amalgam, a fissure sealant resin, a composite bonding material, an orthodontic appliance, a dental prosthetic, a resin varnish, and an oral surgery implant.

25. The method as recited in claim 2, wherein the composition comprises at least one pellet that may be attached to a tooth using dental cement.

26. A method of treating sensitive teeth comprising:

attaching a fluoride releasing glass composition to a person's tooth, wherein the glass composition is formed by combining and melting a phosphorus oxide and at least one of sodium, potassium, lithium or aluminum in oxide and/or fluoride form, wherein the glass composition has the general empirical formula given below, expressed in approximate weight percent of each element:

phosphorus: 16-24 fluorine: 5-30 oxygen: 20-40 wherein the glass composition includes up to about 5 weight percent of boron and/or silicon; and allowing a therapeutically effective amount of fluoride to be slowly released over time as the glass composition is exposed to saliva within the person's mouth in order for the fluoride to contact tooth surfaces and thereby reduce chronic and/or acute tooth sensitivity.

* * * * *